United States Patent [19]
Conrads et al.

[11] Patent Number: 5,808,158
[45] Date of Patent: Sep. 15, 1998

[54] PRODUCTION OF PRIMARY GUERBET AMINES

[75] Inventors: Martin Conrads, Moers; Albert Thomas Hermann; Erich Scherf, both of Brunsbüttel; Arwed Wagner, Köln, all of Germany

[73] Assignee: RWE-DEA Aktiengesellschaft für Mineraloel und Chemie, Germany

[21] Appl. No.: 647,355

[22] Filed: May 9, 1996

[30] Foreign Application Priority Data

May 9, 1996 [DE] Germany .................. 195 16 490.9

[51] Int. Cl.⁶ .................................................. C07C 209/02
[52] U.S. Cl. ........................... 564/480; 564/478; 564/479
[58] Field of Search .................... 564/478, 479, 564/480

[56] References Cited

U.S. PATENT DOCUMENTS

| | | | |
|---|---|---|---|
| 3,128,311 | 4/1964 | Shirley et al. | 260/585 |
| 3,390,184 | 6/1968 | Moss et al. | 260/585 |
| 4,409,399 | 10/1983 | Swift et al. | 564/473 |
| 4,760,190 | 7/1988 | Twigg | 564/480 |
| 5,166,433 | 11/1992 | Irgang et al. | 564/106 |
| 5,530,127 | 6/1996 | Reif et al. | 544/106 |

FOREIGN PATENT DOCUMENTS

| | | |
|---|---|---|
| 1953263 | 10/1969 | Germany . |
| 1953263 | 2/1972 | Germany . |
| 2625945 | 6/1976 | Germany . |
| 2625945 | 2/1977 | Germany . |

*Primary Examiner*—Brian M. Burn
*Attorney, Agent, or Firm*—Madan & Morris

[57] ABSTRACT

A process for producing primary amines which comprises reacting primary alcohols branched in position 2 with ammonia in the presence of a metal catalyst/co-catalyst.

21 Claims, No Drawings

PRODUCTION OF PRIMARY GUERBET AMINES

The instant invention relates to a process for producing primary amines which comprises reacting primary alcohols branched in position 2, termed Guerbet alcohols, with ammonia in the liquid phase at elevated temperature and under pressure in the presence of a metal catalyst/catalyst mixture.

Primary and secondary fatty amines are important raw materials for surfactants, emulsifiers, and microbiocides based on quaternary ammonium salts. The physical properties of the finished products can be improved by incorporating branched alkyl residues which have the effect of lowering the melting point. While this effect can also be achieved by branched methyl, longer-chain branching in α-position to the amine function would allow further improvements of the properties of the end products. The use of said amines as raw materials for textile finishing has a favorable effect on the absorption of water which is shown by improved antistatic properties and higher wear comfort of the textiles treated in this way (cf. German application DE-OS 2625945). Furthermore, the bactericidal and fungicidal effects of the ammonium salts are significantly increased by the alkyl branched in α-position to the ammonium function (cf. Japanese application JP 63096102) such that effective microbiocides are obtained which may be used both as disinfectants, wood preservatives, and protective architectural coatings. Another important field of application for α-branched amines is that of amine oxides which are mild to the skin and, therefore, are used e.g. as surfactants in body care products.

Primary alkyl amines with long-chain alkyl residues, such as the isofol amines described herein, are used among others as flotation auxiliaries, oilfield chemicals or corrosion inhibitors. Furthermore, primary amines can be useful as synthesis building blocks for a large number of derivatives, such as fatty amine ethoxylates (emulsifiers and dispersants), betains and amine oxides (detergents), and quaternary ammonium compounds (biocides, antistatics).

The reaction of ammonia with primary, long-chain alcohols is known. A large number of catalysts suitable for said liquid-phase amination of fatty alcohols with ammonia have been disclosed, e.g. in U.S. Pat. No. 4,409,399 describing the state of the art of liquid-phase amination processes. By 'liquid phase' we mean an amination process wherein the alcohol is in the liquid phase, while the ammonia or the primary or secondary amines are in the liquid or gaseous phase under the reaction conditions defined hereinafter. However, it is difficult to selectively produce a specific amine, especially a primary amine, by reacting an alcohol with ammonia. Normally, secondary and tertiary amines are produced in large quantities whenever the reaction is carried out with the aim of achieving high conversion rates.

A wide variety of metal catalysts are used for the amination of alcohols, e.g. nickel, copper, chromium, cobalt, and iron, or the oxides thereof, optionally in combination with alkali and alkaline earth metals as co-catalysts. A large number of said catalysts are highly reactive which, however, will mean poor selectivities for primary amines.

In German application DE-OS 2625945, there is described the amination of Guerbet alcohols in the presence of a zinc chromium or zinc aluminium catalyst and hydrogen at a temperature of 280° C. to 320° C. and a pressure of 250 to 260 bar. The selectivity for primary amines is not disclosed. In U.S. Pat. No. 4,409,399 copper/nickel/magnesium oxide catalyst systems have been employed for the selective production of secondary fatty amines.

In most cases, high selectivities are only achieved at low conversion rates which, however, is a great disadvantage whenever the primary amine has to be separated from the residual alcohol by subsequent distillation. Especially with Guerbet alcohols, there are some problems associated with the separation of the alcohol and the primary amine by distillation, because the boiling points of said products are close together. On the other hand, when using conventional amination catalysts at higher reaction rates, there will be lower selectivities for primary amines.

It is an object of this invention to provide a process for the selective production of primary amines that are alkyl-branched in position 2 from the corresponding alcohols in the presence of a suitable catalyst system and under appropriate reaction conditions.

We have found, unexpectedly, that high selectivities are achieved in the reaction of Guerbet alcohols with ammonia to yield primary Guerbet amines when employing catalyst/co-catalyst systems comprising certain mixtures of metals or oxides thereof and metal oxides that are different therefrom as co-catalysts.

The process of the invention for producing primary amines by reaction of certain alcohols with ammonia in the presence of a catalyst/catalyst mixture comprises reacting one or more primary alcohol(s) branched in position 2, as defined by the formula

with ammonia, wherein $R^1$ and $R^2$ each represent the same or different aliphatic, saturated and unbranched, cyclic and/or acyclic alkyl residues each of which having from 1 to 17 carbon atoms, and using a supported catalyst/catalyst mixture comprising the metals nickel and/or cobalt and/or the oxides thereof. Furthermore, the catalyst may additionally comprise copper and/or copper oxide.

The catalysts and, optionally, the co-catalysts may be supported on silica gel or silica, alumina and/or graphite, but preferably on $SiO_2$.

The catalysts may be used in conjunction with barium oxide, zirconium oxide and/or zinc oxide as co-catalysts.

Preferably, each of the residues $R^1$ and $R^2$ of the alcohol(s) represents the same or different aliphatic, saturated and unbranched, acyclic alkyl residue having from 3 to 17 carbon atoms, said alcohol(s) having, in total, from 12 to 36 carbon atoms.

Said alcohols may be reacted with ammonia in the liquid phase, the reaction temperature being 100° to 350° C., preferably 230° to 270° C. The molar ratios of ammonia to alcohol can be in the range of 2.5:1 to 5:1, but preferably in the range of 3:1 to 3.5:1.

The activity of the catalyst/catalyst mixture and, optionally, one or more co-catalyst(s) may be increased by using hydrogen prior to or during the reaction. The alcohols are preferably reacted with ammonia in a reducing hydrogen atmosphere employing a hydrogen excess pressure of from 1.05 to 40 bar, preferably from 20 to 40 bar.

In an embodiment of the process of the instant invention, an α-branched alcohol having from 12 to 36 carbon atoms is charged to a high-pressure autoclave along with the catalyst, after which the air in the reactor is displaced by nitrogen and liquid ammonia is charged to the autoclave. At room temperature the total pressure is adjusted to 20 to 40 bar using hydrogen. Then the reaction vessel is heated to reaction temperature, i.e. 230° to 270° C., the pressure increasing to 100 to 250 bar. The mole ratio of ammonia to alcohol can be in the range of 2.5:1 to 5:1, but preferably in the range of 3:1 to 3.5:1.

Once the reaction is complete, the autoclave is cooled and the products are further treated employing standard methods. The reaction may be carried out either discontinuously or continuously.

Examples of catalysts that can be used herein include Ni/NiO (Südchemie AG, G49BRS) and Co/CoO (Südchemie AG, G67BRS) supported on silica (cf. Table 1) and a metal/metal oxide catalyst containing 42 wt. % nickel, 4 wt. % cobalt and 4 wt. % copper supported on kieselguhr (Mallinckrodt E-221P).

TABLE 1

Composition of Catalysts Used in Examples 1 to 3

| Catalysts | | Composition [wt. %]* | | |
|---|---|---|---|---|
| G67BRS | I | Co/CoO (≈Σ 60%) | ZrO₂ | SiO₂ |
| G49BRS | II | Ni (35%)/NiO (18%) | C (3%) | SiO₂ (30%) |

*according to the manufacturer, Südchemie AG

Other catalysts/co-catalysts, such as palladium/activated charcoal (Aldrich), copper chromite (E-106P, Mallinckrodt), Cu/Zn (E-320P, Mallinckrodt), and the unsupported nickel catalyst E-480D (Mallinckrodt) have not proved to be suitable for the selective conversion of Guerbet alcohols into primary amines.

EXAMPLES

The reaction was carried out according to this invention by bringing together the alcohol and the ammonia in the presence of a suitable catalyst under the conditions defined above. The catalyst may be activated either in situ or in a preceding activation step in a reducing atmosphere at temperatures of between 150° C. and 300° C. In order to obtain the desired higher amine, water and unreacted ammonia, if any, were removed from the reaction vessel by rapid distillation. After separation of the heterogeneous catalyst from the residual reaction mixture, the desired amine was distilled off. The residue remaining in the distillation flask consisted of the condensation products, heavies and unreacted alcohol.

EXAMPLES 1, 2 AND 3

One mole of Guerbet alcohol and 3 grams of catalyst I (G67BRS from Südchemie) were charged to an autoclave. The reaction system was purged with an inert gas, after which 60 grams of liquefied ammonia were added. Then the pressure was adjusted to 20 bar using hydrogen and the reaction vessel was heated to 270° C. while stirring. After 4 hours at this temperature, the reaction vessel was cooled to ambient temperature and the pressure was released. Excess ammonia was expelled in the nitrogen flow by heating to 50° C. after which the pure amines were isolated by fractionated distillation. In example 3, catalyst II (G49BRS) was used for the process.

TABLE 2

Amination of Different Guerbet Alcohols

| Exp. No. | Alcohol Feed | Catalyst | Con- version | Composition of the Crude Product [area % by GC] | | |
|---|---|---|---|---|---|---|
| | | | | Prim. Amines | Sec. Amines | Others* |
| 1 | 2-Hexyldecanol | I | 93% | 80.6 | 6.8 | 12.6 |
| 2 | 2-Octyldodecanol | I | 91.7% | 83.5 | 5.5 | 11 |
| 3 | 2-Decyltetra- decanol | II | 97% | 88 | — | 12 |

*residual alcohol, tert. amines, amides, nitriles

We claim:

1. A process for producing primary amines by reacting alcohols with ammonia in the presence of a catalyst/catalyst mixture which comprises the steps of
    (A) reacting at least one primary alcohol branched in position 2, as defined by the formula

wherein $R^1$ and $R^2$ each represent the same or different aliphatic, saturated and unbranched cyclic and/or acyclic alkyl residues each having from 1 to 17 carbon atoms, with ammonia and
    (B) using a supported catalyst/catalyst mixture comprising the metals nickel and/or cobalt and/or the oxides thereof.

2. The process of claim 1 wherein said alcohol is reacted in the presence of a catalyst/catalyst mixture on a support selected from the group consisting of silica, alumina and charcoal.

3. The process according to claim 1 wherein said alcohol is reacted in the presence of a catalyst/catalyst mixture additionally comprising copper and/or copper oxide.

4. The process according to claim 1 wherein said alcohol is reacted in the presence of at least one additional co-catalyst selected from the group consisting of zirconium oxide, barium oxide and/or zinc oxide.

5. The process of claim 1 which comprises reacting the alcohol as defined by general formula I, wherein $R^1$ and $R^2$ each represent the same or different aliphatic, saturated and unbranched, acyclic alkyl residues each having from 3 to 17 carbon atoms and said alcohol has, in total, 12 to 36 carbon atoms.

6. The process according to claim 1 wherein the reaction with ammonia is carried out in the liquid phase.

7. The process according to claim 1 wherein the reaction is carried out at a temperature in the range of 100° to 350° C.

8. The process according to claim 1 wherein the reaction is carried out in the presence of a catalyst/catalyst mixture that has been activated with hydrogen prior to or during the reaction.

9. The process according to claim 1 wherein the reaction is carried out in a reducing hydrogen atmosphere in which the hydrogen has an excess pressure of 1.05 to 40 bar.

10. The process of claim 1 where the molar ratio of ammonia to alcohol is in the range from 2.5:1 to 5:1.

11. A process for producing primary amines by reacting alcohols with ammonia in the presence of a catalyst/catalyst mixture which comprises the steps of
    (A) reacting at least one primary alcohol branched in position 2, as defined by the formula $$\begin{array}{cc} R^2 & OH \\ | & | \\ R^1-CH-CH_2, \end{array} \quad (I)$$

wherein $R^1$ and $R^2$ each represent the same or different aliphatic, saturated and unbranched cyclic and/or acyclic alkyl residues each having from 1 to 17 carbon atoms, with ammonia in the liquid phase at a temperature in the range of 100° to 350° C., and (B) using a catalyst/catalyst mixture comprising nickel metal, cobalt metal, nickel oxide, or cobalt oxide, supported on a support selected from the group consisting of silica, alumina and charcoal.

12. The process according to claim 11 wherein said alcohol is reacted in the presence of a catalyst/catalyst mixture additionally comprising copper and/or copper oxide.

13. The process according to claim 11 wherein said alcohol is reacted in the presence of at least one additional co-catalyst selected from the group consisting of zirconium oxide, barium oxide and zinc oxide.

14. The process of claim 11 which comprises reacting the alcohol as defined by general formula I, wherein $R^1$ and $R^2$ each represent the same or different aliphatic, saturated and unbranched, acyclic alkyl residues each having from 3 to 17 carbon atoms and said alcohol has, in total, 12 to 36 carbon atoms.

15. A process according to claim 11 wherein the reaction is carried out in the presence of a catalyst/catalyst mixture that has been activated with hydrogen prior to or during the reaction.

16. A process according to claim 11 wherein the reaction is carried out in a reducing hydrogen atmosphere in which the hydrogen has an excess pressure of 1.05 to 40 bar.

17. A process for producing primary amines by reacting alcohols with ammonia in the presence of a catalyst/catalyst mixture which comprises the steps of (A) reacting at least one primary alcohol branched in position 2, as defined by the formula $$\begin{array}{cc} R^2 & OH \\ | & | \\ R^1-CH-CH_2, \end{array} \quad (I)$$

wherein $R^1$ and $R^2$ each represent the same or different aliphatic, saturated and unbranched acyclic alkyl residues each having from 3 to 17 carbon atoms, in total, 12 to 36 carbon atoms, with ammonia in the liquid phase at a temperature in the range of 100° to 350° C., and (B) using a catalyst/catalyst mixture selected from the group consisting of nickel metal, cobalt metal, copper metal, nickel oxide, cobalt oxide and copper oxide, together with a co-catalyst selected from the group consisting of zirconium oxide, barium oxide and zinc oxide, supported on a support selected from the group consisting of silica, alumina and charcoal.

18. A process according to claim 17 wherein the reaction is carried out in the presence of a catalyst/catalyst mixture that has been activated with hydrogen prior to or during the reaction.

19. A process according to claim 17 wherein the reaction is carried out in a reducing hydrogen atmosphere in which the hydrogen has an excess pressure of 1.05 to 40 bar.

20. The process of claim 17 where the molar ratio of ammonia to alcohol is in the range from 2.5:1 to 5:1.

21. A process according to claim 17 wherein the catalyst is selected from the group consisting of cobalt metal and cobalt oxide, together with zirconium oxide as a co-catalyst; and nickel metal and nickel oxide.

* * * * *